(12) United States Patent
Chizh et al.

(10) Patent No.: US 7,034,041 B2
(45) Date of Patent: Apr. 25, 2006

(54) SUBSTITUTED 4-PHENYL-1-(1-PHENYLCYCLOHEXYL)-1,2,3,6-TETRAHYDROPYRIDINE

(75) Inventors: Boris Chizh, Aachen (DE); Michael Sattlegger, Bonn (DE); Claudia Hinze, Aachen (DE); Bernd Sundermann, Aachen (DE); Angelika Kerwer-Thomas, Aachen (DE); Gisela Henn, Simmerath (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 10/382,935

(22) Filed: Mar. 7, 2003

(65) Prior Publication Data

US 2003/0225116 A1 Dec. 4, 2003

Related U.S. Application Data

(63) Continuation of application No. PCT/EP01/10224, filed on Sep. 5, 2001.

(30) Foreign Application Priority Data

Sep. 8, 2000 (DE) ............... 100 44 649

(51) Int. Cl.
*A61K 31/445* (2006.01)
*C07D 211/02* (2006.01)

(52) U.S. Cl. ............ 514/315; 514/278; 546/185; 546/192; 546/194

(58) Field of Classification Search .......... 546/185, 546/192, 194; 514/315, 278
See application file for complete search history.

(56) References Cited

FOREIGN PATENT DOCUMENTS

WO    WO 00/06545    2/2000

OTHER PUBLICATIONS

Itzhak et al., "New Analgesic Drugs Derived from Phencyclidine", *J. Med. Chem.*, vol. 24, No. 5 (1981), pp. 496-499.
Raffa et al., "Complementary and Synergistic Antinociceptive Interaction Between the Enantiomers of Tramadol", *The Journal of Pharmacology and Experimental Therapeutics*, vol. 267, No. 1 (1993), pp. 331-340.
Al-Deeb, "Synthesis and Analgesic Activity of New Phencyclidine Derivatives", *Arzneimittal Forschung*, vol. 44, No. 10 (1994), pp. 1141-1144.

*Primary Examiner*—Rita Desai
(74) *Attorney, Agent, or Firm*—Crowell & Moring LLP

(57) ABSTRACT

Substituted 4-phenyl-1-(1-phenylcyclohexyl)-1,2,3,6-tetrahydropyridine (compounds), methods for the production thereof, pharmaceutical compositions containing said compounds, and methods of treatment of pain and other diseases using the pharmaceutical compositions.

19 Claims, No Drawings

SUBSTITUTED 4-PHENYL-1-(1-PHENYLCYCLOHEXYL)-1,2,3,6-TETRAHYDROPYRIDINE

CROSS REFERENCE TO RELATED APPLICATIONS

The present application is a continuation of International Patent Application No. PCT/EP01/10224, filed Sep. 5, 2001, designating the United States of America and published in German as WO 02/20481, the entire disclosure of which is incorporated herein by reference. Priority is claimed based on Federal Republic of Germany Patent Application No. 100 44 649.3, filed Sep. 8, 2000.

BACKGROUND AND SUMMARY OF THE INVENTION

The invention relates to substituted 4-phenyl-1-(1-phenylcyclohexyl)-1,2,3,6-tetrahydropyridines, a process for their production, medicaments containing these compounds, the use of these substances for the production of medicaments as well as method for treating pain using the medicaments.

Pain is one of the main symptoms in clinical practice, and there is a worldwide demand for effective pain treatment. The urgent practical need for a patient-oriented and targeted treatment of chronic and non-chronic painful conditions, which treatment in this context means the successful and satisfactory treatment of pain in patients, is documented in the large number of scientific articles that have recently appeared in the field of applied analgesics or in basic research on nociception. Thus, phencyclidine derivatives having an analgesic action are known for example from J. Med. Chem. 1981, 24, 469–499 and Arzneim.-Forsch./Drug Res. 44(II), No. 10 (1994), 1141–1144.

In WO 00/06545 compounds are described that have a high affinity for the nociceptin receptor ORL-1 and are likewise suitable for relieving pain.

Conventional opioids, such as morphine, are effective in treating severe to very severe pain. There are, however, numerous undesirable side effects including respiratory depression, vomiting, sedation, constipation as well as development of tolerance. Furthermore, they are less effective in treating neuropathic or incidental pain such as that which frequently occurs in patients with tumors.

Tramadol hydrochloride—(1RS,2RS)-2-[(dimethylamino)-methyl]-1-(3-methoxyphenyl)-cyclohexanol—occupies on the central nervous system, since this active substance is very effective in blocking pain without exhibiting the known side effects of opioids (J. Pharmacol. Exptl. Ther. 267, 33 (1993)).

Knowledge of the physiological importance of ion channel-selective substances has been obtained by the development of the patch-clamp technique. Of particular importance is the NMDA ion channel, through which a substantial proportion of synapse communications takes place. The exchange of calcium ions between a neuronal cell and its environment is controlled by this ion channel. The action of NMDA antagonists on the inflow of calcium ions into the cell interior has been detected by means of the patch-clamp technique.

In the unactivated state, the NMDA ion channels are in each case closed by individual magnesium ions that are located in the interior of the channel, and ions cannot pass through the channel due to their size. In the activated state the smaller calcium and sodium ions can pass through the channel. The (+)-MK801 binding site of the NMDA ion channel (ionotropic NMDA receptor) is also located in the interior of this membrane protein. Substances with an NMDA-antagonistic action, such as phencyclidine (PCP), ketamine or MK801, occupy this binding site (so-called channel blockers) and thus close the relevant NMDA ion channel.

NMDA ion channels play an important role in many physiological and pathophysiological processes, such as in epilepsy, schizophrenia, neurodegenerative diseases, in particular Alzheimer's disease, Huntington's disease and Parkinson's disease, cerebral ischaemias and infarcts, psychoses caused by raised amino acid levels, brain swellings, deficiency states of the central nervous system, in particular in hypoxia and anoxia, AIDS dementia, encephalomyelitis, Tourette's syndrome, perinatal asphyxia and tinnitus.

The object of the invention was accordingly to provide analgesically active substances that are suitable for treating severe pain, in particular for treating chronic and neuropathic pain. In this connection they should exhibit both a μ-agonistic agonistic and an NMDA-antagonistic action. Furthermore these active substances should have as few as possible of the side effects of opioid analgesics, such as nausea, vomiting, dependency, respiratory depression and constipation.

According to the invention this object is achieved by substituted 4-phenyl-1-(1-phenylcyclohexyl)-1,2,3,6-tetrahydropyridines of formula I. These compounds have an excellent analgesic action.

The invention accordingly provides substituted 4-phenyl-1-(1-phenylcyclohexyl)-1,2,3,6-tetrahydropyridines of formula I,

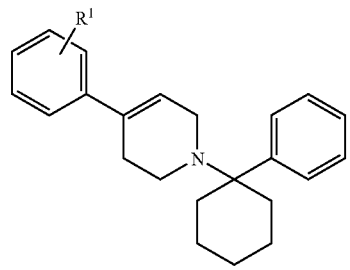

I wherein $R^1$ denotes $C_1$–$C_5$-alkyl (branched or unbranched), halogen (except 4-Cl), O—$C_1$–$C_5$-alkyl (branched or unbranched), S—$C_1$–$C_5$-alkyl (branched or unbranched), and/or their salts of physiologically compatible or acceptable acids.

In preferred compounds $R^1$ denotes methyl, chlorine (except in the 4-position), fluorine, methoxy or methylsulfanyl.

Particularly preferred are the following substituted 4-phenyl-1-(1-phenylcyclohexyl)-1,2,3,6-tetrahydropyridines:

4-(2-fluorophenyl)-1-(1-phenylcyclohexyl)-1,2,3,6-tetrahydropyridine or the corresponding hydrochloride (1)

4-(3-fluorophenyl)-1-(1-phenylcyclohexyl)-1,2,3,6-tetrahydropyridine or the corresponding hydrochloride (2)

4-(4-fluorophenyl)-1-(1-phenylcyclohexyl)-1,2,3,6-tetrahydropyridine or the corresponding hydrochloride (3)

4-(2-methoxyphenyl)-1-(1-phenylcyclohexyl)-1,2,3,6-tetrahydropyridine or the corresponding hydrochloride (4)

4-(3-methoxyphenyl)-1-(1-phenylcyclohexyl)-1,2,3,6-tetrahydropyridine or the corresponding hydrochloride (5)

4-(4-methoxyphenyl)-1-(1-phenylcyclohexyl)-1,2,3,6-tetrahydropyridine or the corresponding hydrochloride (6)

4-(2-methylphenyl)-1-(1-phenylcyclohexyl)-1,2,3,6-tetrahydropyridine or the corresponding hydrochloride (7)

4-(3-methylphenyl)-1-(1-phenylcyclohexyl)-1,2,3,6-tetrahydropyridine or the corresponding hydrochloride (8)

4-(4-methylphenyl)-1-(1-phenylcyclohexyl)-1,2,3,6-tetrahydropyridine or the corresponding hydrochloride (9)

4-(2-methylsulfanylphenyl)-1-(1-phenylcyclohexyl)-1,2,3,6-tetrahydropyridine or the corresponding hydrochloride (10)

4-(2-chlorophenyl)-1-(1-phenylcyclohexyl)-1,2,3,6-tetrahydropyridine or the corresponding hydrochloride (11).

The invention also provides a process for the production of substituted 4-phenyl-1-(1-phenylcyclohexyl)-1,2,3,6-tetrahydropyridines of formula I, which may be variously substituted by $R^1$.

The production of the compounds according to the invention is carried out in the following stages:

The enamine IV is formed from cyclohexanone II and 1,4-dioxa-8-aza-spiro[4.5]decane III.

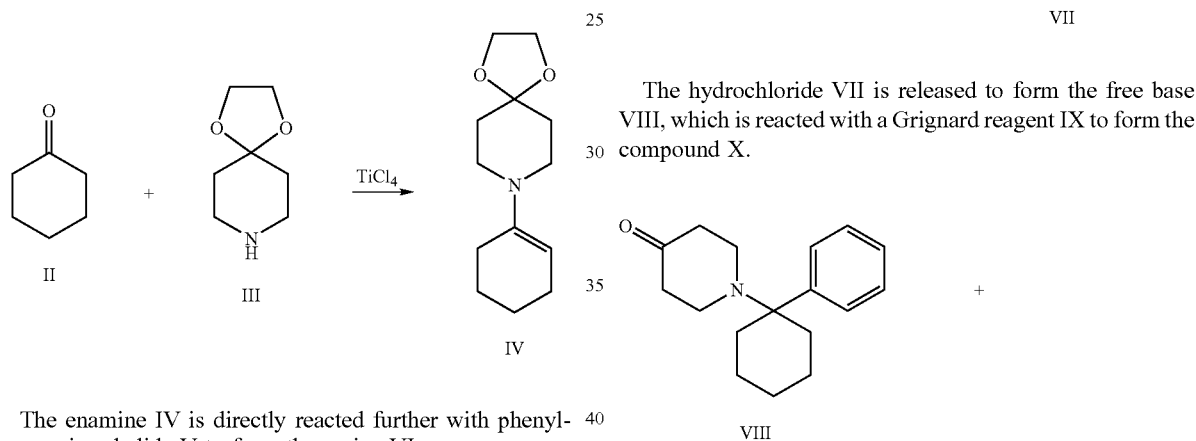

The enamine IV is directly reacted further with phenylmagnesium halide V to form the amine VI:

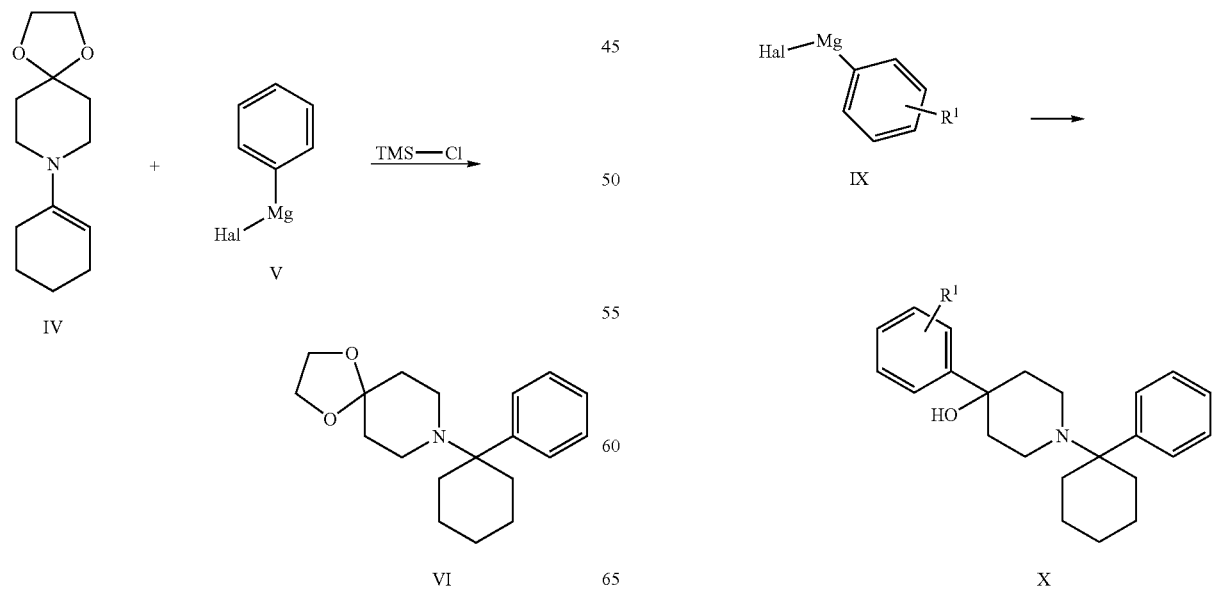

The amine VI is hydrolyzed in a further stage and compound VII is precipitated as hydrochloride.

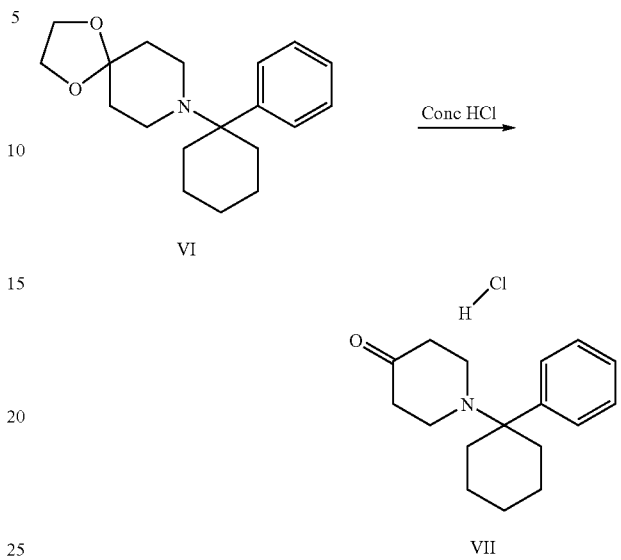

The hydrochloride VII is released to form the free base VIII, which is reacted with a Grignard reagent IX to form the compound X.

After precipitation of the compounds X as hydrochlorides XI, the latter can be reacted further with formic acid to form the compounds I according to the invention.

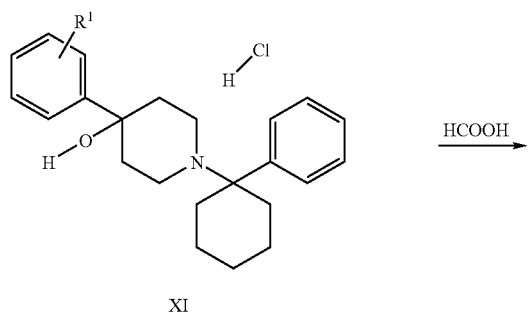

XI

HCOOH →

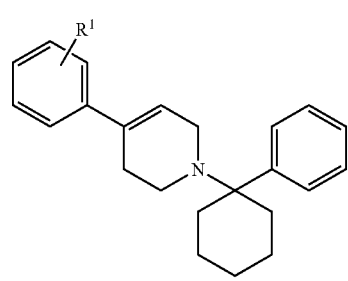

I

According to a particularly preferred variant of the preceding process, in stage 2, i.e. the Grignard reaction, the enamine IV is reacted further directly in the presence of ethereal HCl with phenylmagnesium halide V that was previously introduced, to form the amine VI, which can be obtained in a higher and more reproducible yield in this way than by the aforedescribed process.

A further preferred process variant is carried out as follows:

The aminonitrile XII is formed from cyclohexanone II and 1,4-dioxa-8-aza-spiro[4.5]decane III in the presence of potassium cyanide and hydrochloric acid.

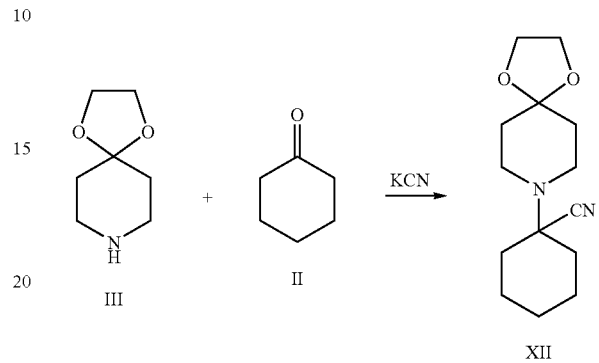

The compound XII is reacted with phenyl Grignard reagents to form the amine VI.

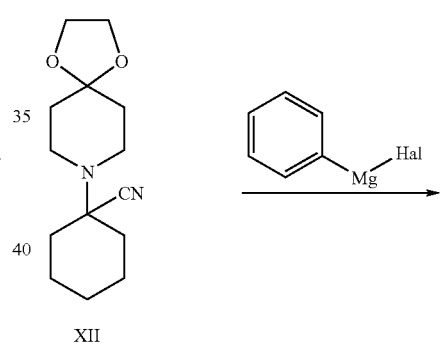

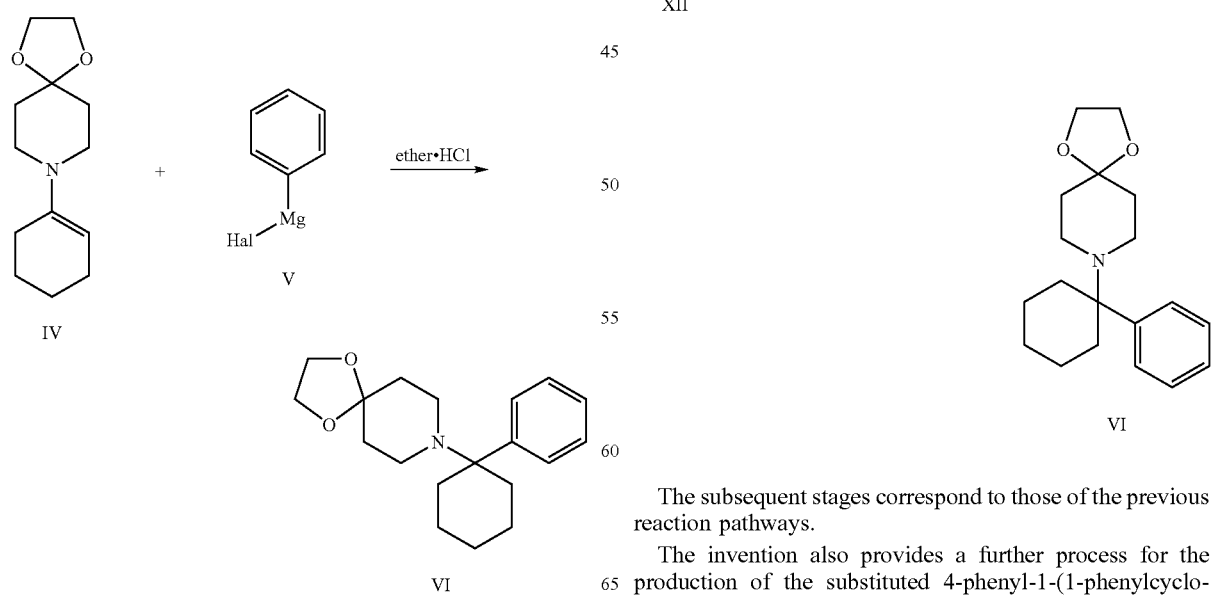

The subsequent stages correspond to those of the previous reaction pathways.

The invention also provides a further process for the production of the substituted 4-phenyl-1-(1-phenylcyclohexyl)-1,2,3,6-tetrahydropyridines of formula I that may be variously substituted with $R^1$, in which the compound XIV is first formed from N-tert.-butyloxycarbonyl-4-piperidone XIII and Grignard reagent IX:

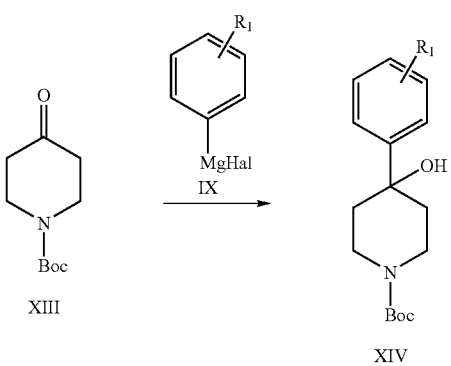

The tert.-butyloxycarbonyl protective group is split off from the compound XIV with an acid, preferably HCl, HBr or HBr/glacial acetic acid or formic acid, with the elimination of water. The compound XV is thereby formed as the HCl salt:

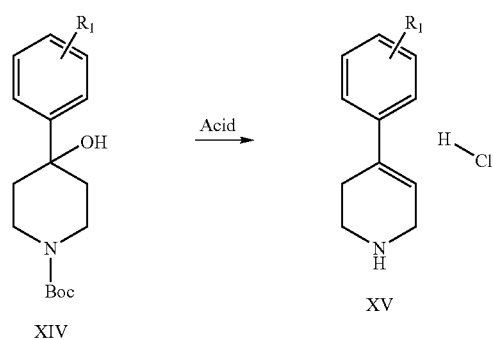

Compound XV is reacted with titanium(IV) chloride and cyclohexanone II to form the corresponding enamine XVI:

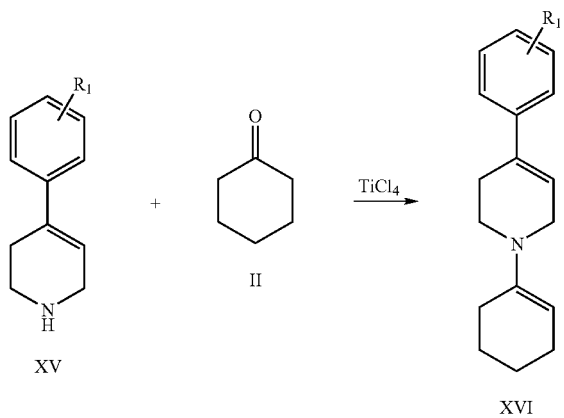

The enamine XVI is reacted in the presence of trimethylchlorosilane or ethereal HCl with phenylmagnesium halide (preferably chloride or bromide).

The HCl salt of the resultant compound of formula I is then precipitated.

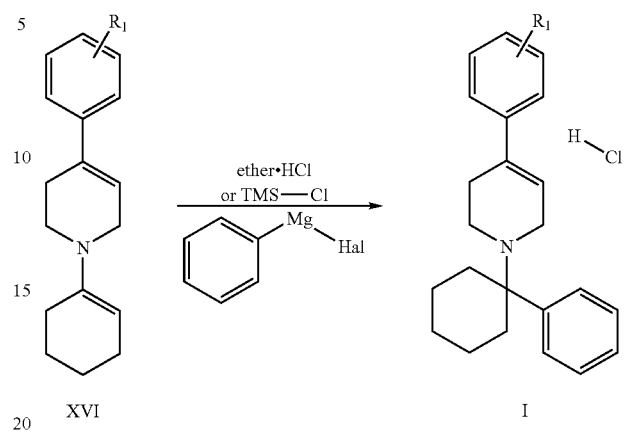

The compounds of formula I can be converted into their salts in a manner well known to those in the art using physiologically compatible acids, for example hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid and/or aspartic acid. The salt formation is preferably carried out in a solvent, for example diethyl ether, diisopropyl ether, alkyl esters of acetic acid, acetone, and/or 2-butanone. Trimethylchloro-silane in methyl ethyl ketone is furthermore suitable for the preparation of the hydrochlorides.

The substituted 4-phenyl-1-(1-phenylcyclohexyl)-1,2,3,6-tetrahydropyridines according to the invention of formula I are non-toxic and thus are suitable pharmaceutical active substances.

The invention furthermore provides medicaments containing as active substance at least one substituted 4-phenyl-1-(1-phenylcyclohexyl)-1,2,3,6-tetrahydropyridine of formula I, or at least a salt thereof of physiologically compatible acids.

The invention accordingly also provides for the use of at least one substituted 4-phenyl-1-(1-phenylcyclohexyl)-1,2,3,6-tetrahydropyridine of formula I and/or their salts of physiologically compatible acids for the production of medicaments to treat pain, epilepsy, and/or schizophrenia and/or neurodegenerative diseases, in particular Alzheimer's disease, Huntington's disease or Parkinson's disease, and/or cerebral ischaemias and/or cerebral infarcts and/or psychoses caused by raised amino acid levels and/or brain swellings and/or deficiency states of the central nervous system, in particular hypoxia and/or anoxia, and/or AIDS dementia and/or encephalomyelitis and/or Tourette's syndrome and/or perinatal asphyxia and/or tinnitus and/or for the prophylaxis of strokes.

For the preparation of corresponding pharmaceutical formulations there are used, in addition to at least one substituted 4-phenyl-1-(1-phenylcyclohexyl)-1,2,3,6-tetrahydropyridine of formula I, or a salt thereof, carrier materials, fillers, solvents, diluents, colorants and/or binders. The choice of auxiliary substances, as well as the amounts thereof to be used, depends on whether the medicament is to be administered orally, intravenously, intraperitoneally, intradermally, intramuscularly, intranasally, buccally or topically, for example in the treatment of infections of the skin, mucous membranes and eyes. For oral application, preparations in the form of tablets, sugar-coated pills, capsules, granules, drops, juices and syrups are suitable, while for parenteral, topical and inhalative application, solutions, suspensions, readily reconstitutable dry preparations as well as sprays are suitable. Compounds according to the invention of formula I in depot form, in dissolved form or in a plaster, optionally with the addition of agents promoting penetration of the skin, are suitable percutaneous application preparations. Orally or percutaneously usable preparation forms permit the delayed release of the compounds according to the invention of formula I.

The amount of active substance to be administered to a patient depends on the patient's weight, on the type of application, medical indications and severity of the condition. Normally 50 to 500 mg/kg body weight of at least one 4-phenyl-1-(1-phenylcyclohexyl)-1,2,3,6-tetrahydropyridine of formula I are administered.

EXAMPLES

General Remarks

The following examples serve to illustrate the invention in more detail, but do not restrict the general scope of the invention.

The yields of the prepared compounds are not optimized.

All melting points are uncorrected.

Unless otherwise specified, petroleum ether having a boiling point range of 50° C. to 70° C. was used. The term ether denotes diethyl ether.

Silica gel 60 (0.040 to 0.063 mm) from E. Merck, Darmstadt, was used as stationary phase for column chromatography.

Thin-layer chromatography investigations were carried out with HPLC precoated plates, silica gel 60 F 254, from E. Merck, Darmstadt.

The mixing ratios of the solvents for all chromatography investigations are always specified in volume/volume.

"Boc" denotes tert.-butyloxycarbonyl.

THF denotes tetrahydrofuran.

Example 1

4-(2-fluorophenyl)-1-(1-phenylcyclohexyl)-1,2,3,6-tetrahydropyridine hydrochloride (1)

1$^{st}$ Stage to form the compound 8-cyclohex-1-enyl-1,4-dioxa-8-aza-spiro[4.5]decane IV. 31 ml of titanium tetrachloride in 0.5 l of n-hexane were then added dropwise at 0° C. within 60 minutes. After the addition the reaction mixture was heated slowly to 20° C. and stirred for a further 24 hours. The precipitate formed was filtered off under suction and discarded. The filtrate was concentrated by evaporation and directly reacted further. The yield was 83 g (0.37 mole, 71%).

2$^{nd}$ Stage

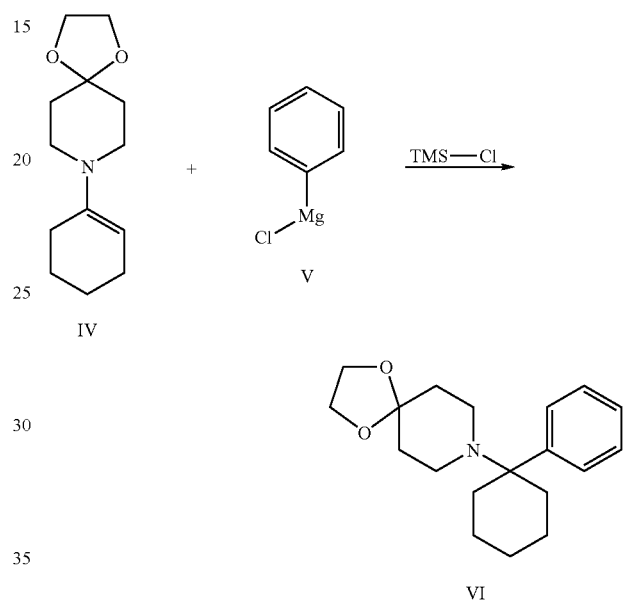

83 g (0.37 mole) of 8-cyclohex-1-enyl-1,4-dioxa-8-aza-spiro[4.5]decane IV were reacted with 200 ml (2 mole) of phenylmagnesium chloride solution V. In addition 52 ml of trimethylchlorosilane in 0.75 l of methylene chloride together with 2 ml of water were introduced and the enamine IV was added dropwise. The Grignard reagent was then added while cooling in an ice bath and the whole was stirred for 3 hours. The reaction mixture was hydrolyzed with 200 ml of ammonium chloride solution and the aqueous phase was extracted with 0.5 l of methylene chloride. The product VI was purified by column chromatography on silica gel using diisopropyl ether. The yield was 36 g (0.12 mole, 32%).

3$^{rd}$ Stage

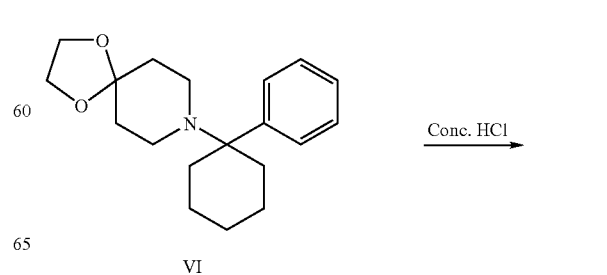

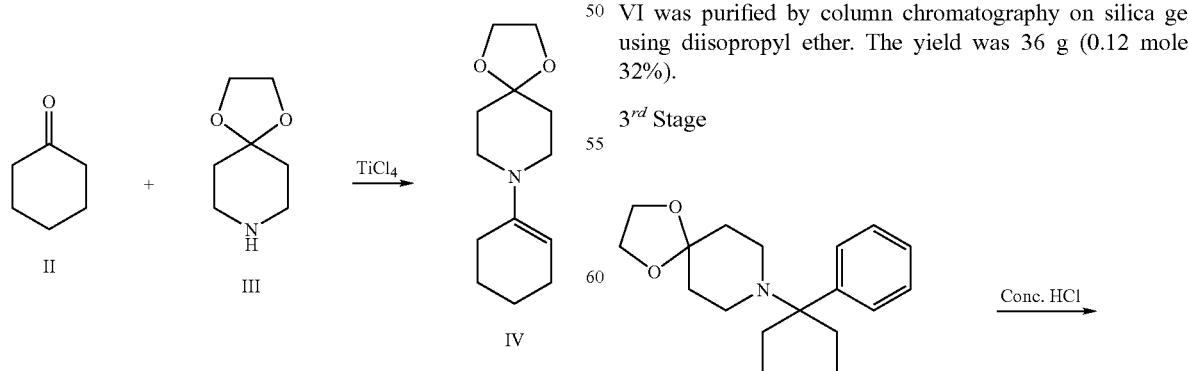

54 ml (0.5 mole) of cyclohexanone together with 200 ml (1.5 mole) of 1,4-dioxa-8-aza-spiro[4.5]decane III were dissolved in 0.5 l of diethyl ether and stirred for half an hour -continued

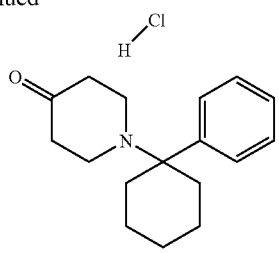

VII

The amine VI was hydrolyzed in a further stage and precipitated as hydrochloride VII. For this purpose 250 ml of concentrated HCl were added at 20° C. to 36 g (0.12 mole) of VI and stirred for 12 hours. The reaction mixture was made alkaline with ammoniacal solution and extracted with diethyl ether. The free base was precipitated as hydrochloride with trimethylchlorosilane. The yield was 21 g (0.072 mole, 60%).

4$^{th}$ Stage

After the release of the hydrochloride VII to form the free base VIII, the latter was reacted with 2-fluorophenyl-magnesium bromide IX to form X and, after precipitation as hydrochloride, to form XI.

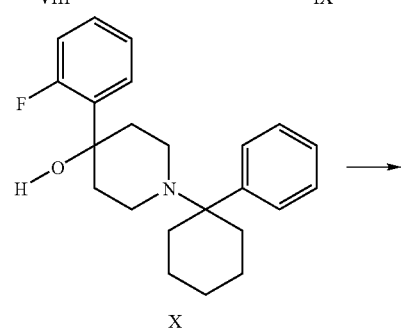

VIII            IX

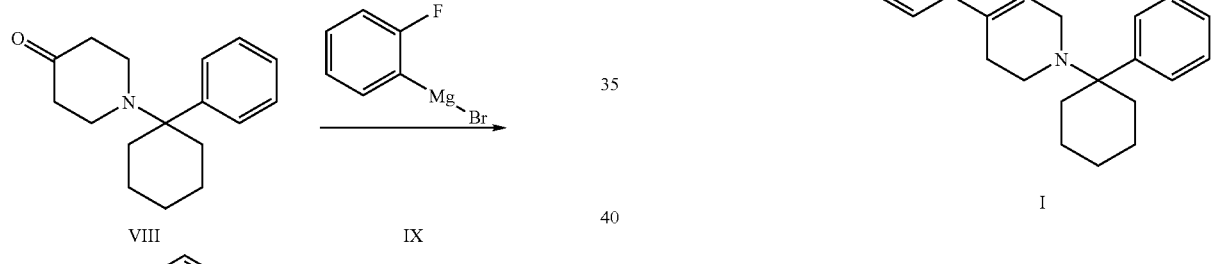

X                                    XI

5th Stage

The hydrochloride XI was heated at 50° C. for 24 hours in formic acid as both solvent and reagent. The formic acid was then removed in vacuo and the residue was stirred in ether. After extraction with ether in alkaline solution and precipitation as hydrochloride with HCl/ether in acetone, the compound 1 was obtained as a colorless solid.

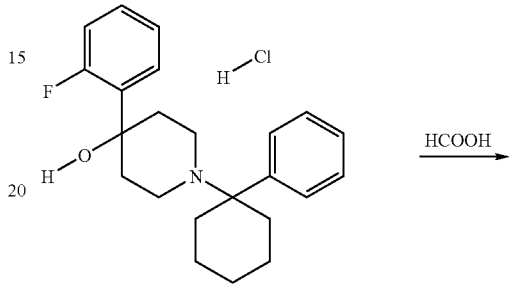

XI

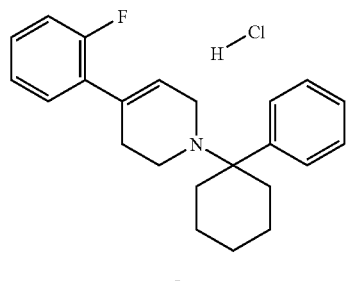

I

A total of 175 mg of product was formed. The melting point of compound 1 was 186° C.

Example 1a

The preparation of the compound 1 was carried out as in Example 1, except that the 2$^{nd}$ stage was altered as follows:

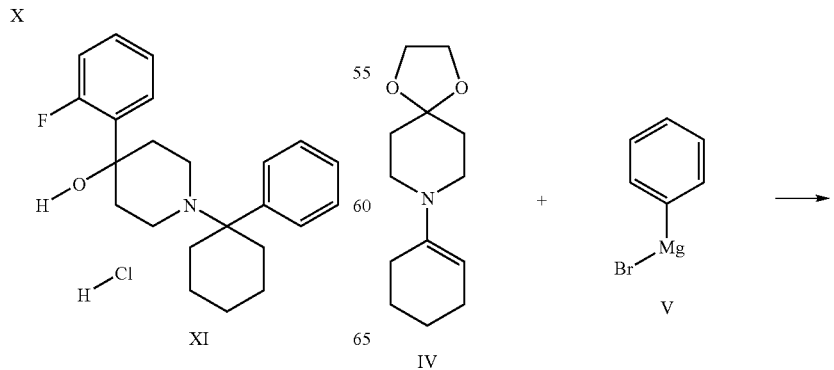

IV                              V

-continued

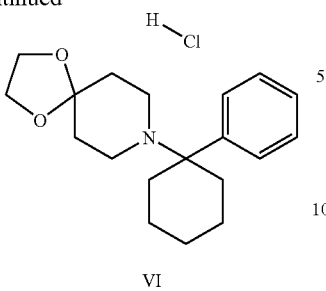

VI 86.3 g (0.386 mole) of 8-cyclohex-1-enyl-1,4-dioxa-8-aza-spiro[4.5]decane IV were added to dichloromethane and cooled to −10° C. to −15° C. 100 ml of 20% ethereal HCl (pH 1) was added dropwise to the solution. This solution was added dropwise over 5 hours to 580 ml of a commercially obtained solution of phenylmagnesium bromide (1 M in THF, corresponding to 0.58 mole). The reaction solution was stirred overnight at room temperature. The solution was then hydrolyzed with about 200 ml of ammonium chloride solution and extracted with dichloromethane. The organic phase was dried with sodium sulfate and evaporated to dryness in vacuo. In order to precipitate the hydrochloride the crude base was dissolved in about 1 l of diethyl ether followed by the addition at 0° C. of 60 ml of ethereal HCl (pH 2–3). The yield was 99.6 g (76%).

Example 1b

The compound 1 is prepared by the second process according to the invention as follows:

$1^{st}$ Stage

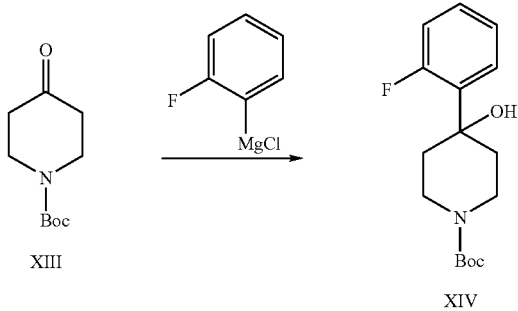

A solution of 11.14 g of 2-fluoroiodobenzene in 25 ml of THF was added dropwise at 0° C. to 27.6 ml of a commercially obtained solution of isopropylmagnesium chloride (2 M in THF). After 15 minutes a solution of 10 g (50.2 mmole) of Boc-piperidone XIII in 25 ml of THF was added. The solution was stirred overnight at room temperature. The solution was then hydrolyzed with about 100 ml of ammonium chloride solution and extracted with diethyl ether. The organic phase was dried with sodium sulfate and evaporated to dryness in vacuo. The crude yield was 15.8 g (quantitative). The compound XIV was reacted further in the crude state, and more specifically once with HCl and once with HBr:

$2^{nd}$ Stage

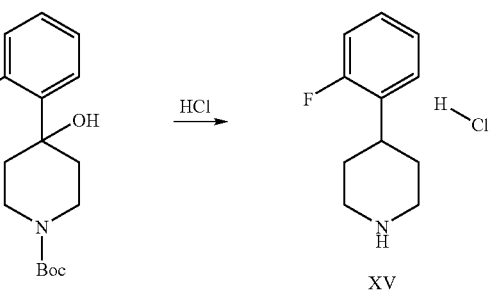

14.2 g (48.08 mmole) of the compound XIV were dissolved in 32% HCl and stirred overnight at room temperature. The aqueous phase, which was originally acidic and then adjusted alkaline with ammonia, was extracted with diethyl ether. The organic phase was dried over sodium sulfate and the solvent was distilled off in vacuo. The crude product was dissolved in an acetone/diethyl ether mixture and the hydrochloride XV was precipitated with ethereal HCl solution. The reaction yield was 3.0 g (29%).

$2^{nd}$ Stage

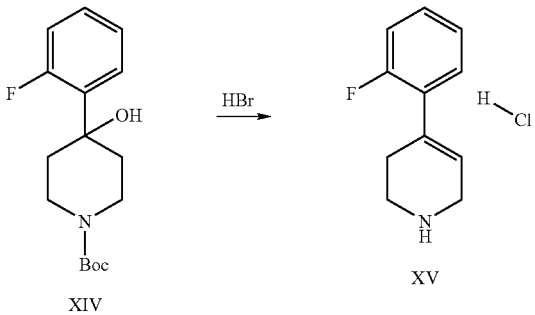

10.6 g (35.89 mmole) of the compound XIV were suspended in about 100 ml of 32% hydrobromic acid and stirred overnight at room temperature. After concentration by evaporation in vacuo, the aqueous phase, which was initially acidic and then adjusted alkaline, was extracted with diethyl ether. The organic phase was dried over sodium sulfate and the solvent was distilled off in vacuo. The crude product was dissolved in an acetone/diethyl ether mixture and the hydrochloride XV was precipitated with ethereal HCl. The reaction yield was 3.9 g (51%).

The further reaction of the hydrochloride XV was carried out as described above for this process.

Example 2

4-(3-fluorophenyl)-1-(1-phenylcyclohexyl)-1,2,3,6-tetrahydropyridine hydrochloride (2)

The preparation of compound 2 was carried out in a similar manner to compound 1. In the fourth stage 3-fluorophenylmagnesium bromide was used instead of 2-fluorophenylmagnesium bromide.

142 mg of compound 2 were obtained. The decomposition temperature is 165° C.

Example 3

4-(4-fluorophenyl)-1-(1-phenylcyclohexyl)-1,2,3,6-tetrahydropyridine hydrochloride (3)

The preparation of compound 3 was carried out in a similar manner to compound 1. In the fourth stage 4-fluorophenylmagnesium bromide was used instead of 2-fluorophenylmagnesium bromide. 300 mg of compound 3 were obtained. The decomposition temperature is 170° C.

Example 4

4-(2-methoxyphenyl)-1-(1-phenylcyclohexyl)-1,2,3,6-tetrahydropyridine hydrochloride (4)

The preparation of compound 4 was carried out in a similar manner to compound 1. In the fourth stage 2-methoxyphenylmagnesium bromide was used instead of 2-fluorophenylmagnesium bromide. 168 mg of compound 4 were obtained. The melting point is 242° C.

Example 5

4-(3-methoxyphenyl)-1-(1-phenylcyclohexyl)-1,2,3,6-tetrahydropyridine hydrochloride (5)

The preparation of compound 5 was carried out in a similar manner to compound 1. In the fourth stage 3-methoxyphenylmagnesium bromide was used instead of 2-fluorophenylmagnesium bromide. 202 mg of compound 5 were obtained. The melting point is 214° C.

Example 6

4-(4-methoxyphenyl)-1-(1-phenylcyclohexyl)-1,2,3,6-tetrahydropyridine hydrochloride (6)

The preparation of compound 6 was carried out in a similar manner to compound 1. In the fourth stage 4-methoxyphenylmagnesium bromide was used instead of 2-fluorophenylmagnesium bromide. 168 mg of compound 6 were obtained. The melting point is 152° C.

Example 7

4-(2-methylphenyl)-1-(1-phenylcyclohexyl)-1,2,3,6-tetrahydropyridine hydrochloride (7)

The preparation of compound 7 was carried out in a similar manner to compound 1. In the fourth stage 2-methylphenylmagnesium bromide was used instead of 2-fluorophenylmagnesium bromide. 160 mg of compound 7 were obtained. The melting point is 199° C.

Example 8

4-(3-methylphenyl)-1-(1-phenylcyclohexyl)-1,2,3,6-tetrahydropyridine hydrochloride (8)

The preparation of compound 8 was carried out in a similar manner to compound 1. In the fourth stage 3-methylphenylmagnesium bromide was used instead of 2-fluorophenylmagnesium bromide. 197 mg of compound 8 were obtained. The melting point is 192° C.

Example 9

4-(4-methylphenyl)-1-(1-phenylcyclohexyl)-1,2,3,6-tetrahydropyridine hydrochloride (9)

The preparation of compound 9 was carried out in a similar manner to compound 1. In the fourth stage 4-methylphenylmagnesium bromide was used instead of 2-fluorophenylmagnesium bromide. 194 mg of compound 9 were obtained. The melting point is 169° C.

Example 10

4-(2-methylsulfanylphenyl)-1-(1-phenylcyclohexyl)-1,2,3,6-tetrahydropyridine hydrochloride (10)

The preparation of compound 10 was carried out in a similar manner to compound 1. In the fourth stage 2-methylsulfanylphenylmagnesium bromide was used instead of 2-fluorophenylmagnesium bromide. 94 mg of compound 10 were obtained. The melting point is 206° C.

Example 11

4-(2-chlorophenyl)-1-(1-phenylcyclohexyl)-1,2,3,6-tetrahydropyridine hydrochloride (11)

The preparation of compound 11 was carried out in a similar manner to compound 1. In the fourth stage 2-chlorophenylmagnesium bromide was used instead of 2-fluorophenylmagnesium bromide. 113 mg of compound 11 were obtained. The melting point is 98° C.

Comparison Example 1

The compound according to Table 6 where $R^{11}$=H and $CH(Z^1)(Z^2)$=benzhydryl from WO 00/06545 (see page 41) was subsequently synthesized.

Comparison Example 2

The compound according to Example 1 from WO 00/06545 (see page 15) was subsequently synthesized.

Pharmacological Investigations

Writing Test in Mice

The analgesic efficacy of the compounds according to the invention was investigated in mice in the phenylquinone-induced writhing test, as modified by I. C. Hendershot, J. Forsaith in J. Pharmacol. Exp. Ther. 125, 237–240 (1959). For this purpose male mice weighing 25 to 30 g were used. Groups of 10 animals per substance dose received 10 minutes after intravenous administration of the test substances, 0.3 ml/mouse of a 0.02% aqueous solution of phenylquinone applied intraperitoneally (phenylbenzoquinone, Sigma, Deisenhofen; preparation of the solution with addition of 5% ethanol and storage in a water bath at 45° C.). The animals were then placed individually in observation cages. Using a push-button counter the number of pain-induced stretching movements (so-called writhing reactions=body contortions with stretching of the rear extremities) were counted 5 to 20 minutes after administration of the phenylquinone. Animals that had received only physiological saline solution with phenylquinone served as control.

All substances were tested in the standard dosage of 10 mg/kg. The percentage inhibition (% inhibition) of the writhing reactions due to a substance was calculated according to the following formula:

$$\% \text{ inhibition} = 100 - \left(\frac{\text{Writhing reaction of treated animals}}{\text{Writhing reaction of control}}\right) \times 100$$

All investigated compounds according to the invention exhibited a moderately strong to strong analgesic action.

The results of selected writhing investigations are summarized in Table 1.

TABLE 1

Analgesia Effect as Determined by Writhing Test in Mice

| Example No. | % Inhibition of the Writhing Reactions 10 mg/kg i.v. |
|---|---|
| 1 | 72 |
| 2 | 98 |
| 3 | 100 |

Molecular Biology Investigations:

μ-Opiate Receptor Binding Investigations a) Determination of the Affinity for the μ-Opiate Receptor in Rats The investigations to determine the affinity of the compounds according to the invention of formula I for the μ-opiate receptor were carried out on brain membrane homogenates (rat brain homogenate without cerebellum, pons and medulla oblongata of male Wistar rats).

For this purpose freshly prepared rat brain was homogenized in 50 mmole/l tris-HCl (pH 7.4) while cooling in ice and centrifuged for 10 minutes at 5,000 g and 4° C. After decanting and discarding the supernatant, and taking up and homogenizing the membrane sediment again in 50 mmole/l tris-HCl (pH 7.4), the homogenate was then centrifuged for 20 minutes at 20,000 g and 4° C. This wash stage was repeated several times. Following this the supernatant was decanted and the membrane sediment was homogenized in cold 50 mmole/l tris-HCl, 20% glycerol (w/v), 0.01% bacitracin (w/v) (pH 7.4) and frozen in aliquots until the testing. For the receptor binding test the aliquots were thawed out and diluted 1:10 with the binding test buffer. In the binding test a 50 mmole/l tris-HCl, 5 mmole/l MgCl (pH 7.4) was used as buffer, and 1 nmole/l of tritiated naloxone was used as radioactive ligand. The results are shown in Table 2.

b) Determination of the Affinity for the Human μ-Opiate Receptor

The receptor affinity for the human μ-opiate receptor was determined in an homogeneous batch in microtitre plates. For this purpose dilution series of the substances to be tested were incubated with a receptor membrane preparation (15–40 μg protein/250 μl incubation batch) of CHO-K1 cells that express the human μ-opiate receptor (RB-HOM-receptor membrane preparation from NEN, Zaventem, Belgium) in the presence of 1 nmole/l of the radioactive ligand [$^3$H]-diprenorphine (NET1121, NEN, Zaventem, Belgium) as well as 1 mg of WGA-SPA beads (wheatgerm agglutinen SPA beads from Amersham/Pharmacia, Freiburg, Germany) in a total volume of 250 μl for 90 minutes at room temperature. 50 mmole/l of tris-HCl supplemented with 0.05% sodium azide and with 0.06% bovine serum albumin was used as incubation buffer. 25 μmole/l of naloxone were added in addition in order to determine the non-specific binding. After the end of the 90-minute incubation period the microtitre plates were centrifuged for 20 minutes at 1000 g and the radioactivity was measured in a β-counter (Microbeta-Trilux, PerkinElmer Wallac, Freiburg, Germany). $IC_{50}$ inhibiting concentrations that produce a 50% displacement of the radioactive ligand were calculated on the basis of the percentage displacement of the radioactive ligand from its binding site on the human μ-opiate receptor by different concentrations of the test substances. $K_i$ values for the test substances were calculated by means of the Cheng-Prusoff equation. The results are shown in Table 3.

NMDA Receptor Binding Investigations

The investigations to determine the NMDA antagonistic action of the respective compound of formula I were carried out on brain membrane homogenates (rat brain homogenate without cerebellum, pons and medulla oblongata of male Wistar rats (Charles River, Sulzfeld, Germany)).

For this purpose freshly prepared rat brains were digested, after removing the cerebellum, pons and medulla oblongata, in 50 mmole/l tris/HCl (pH 7.7) using a Polytron homogenizer (model PT3000, Kinematika AG, Littau, Switzerland) at 6,000 revolutions per minute (r.p.m.) for 1 minute while cooling in ice and then centrifuged for 15 minutes at 4° C. and 60,000 g. After decanting and discarding the supernatant, taking up the membrane pellet again in 50 mmole/l tris/HCl (pH 7.7) and digesting with a homogenizer at 2,000 r.p.m. for 1 minute, the pellet was re-centrigued for 15 minutes at 4° C. and 60,000 g. The supernatant was again discarded and the membrane pellet was homogenized in 50 mmole/l tris/HCl (pH 7.7) (2,000 r.p.m. for 1 minute) and frozen in aliquots at −70° C.

For the receptor binding test aliquots were thawed out and then centrifuged for 15 minutes at 4° C. and 60,000 g. After decanting and discarding the supernatant the membrane pellet was taken up with binding test buffer and homogenized for the binding test (2,000 r.p.m. for 1 minute). 5 mmole/l tris/HCl (pH 7.7) supplemented with 30 μmole/l glycine and 100 μmole/l glutamic acid were used as binding test buffer.

1 nmole/l ($^3$H)-(+)-MK801 ((5R,10S)-(+)-5-methyl-10, 11-dihydro-5H-dibenzo(a,d)cyclohepten-5,10-imine (NET-972, NEN, Cologne, Germany) was added as radioactively labelled ligand. The proportion of non-specific binding was determined in the presence of 10 μmole/l of non-radioactively labelled (+)-MK801 (RBI/Sigma, Deisenhofen, Germany). In further assays the respective compounds of formula I were added in various concentration ranges and the displacement of the radioactive ligand from its specific binding on the NMDA receptor was determined. All assays were carried out in triplicate. The assays were incubated in each case for 40 minutes at 25° C. in a water bath and then harvested by filtration through a glass fibre filter (GF/B) (Whatman GF/B type, Hassel, Munich, Germany) for the determination of the radioactive ligand bound to the brain membrane homogenate. The radioactivity retained by the glass fibre filter discs was measured in a β-counter (Packard TRI-CARB Liquid Scintillation Analyzer 2000CA, Packard Instrument, Meriden, Conn. 06450, USA) after adding a scintillator ("Ready Protein"), Beckmann Coulter GmbH, Krefeld, Germany).

The percentage inhibition calculated from assays in triplicate, of the specific binding of the ligand ($^3$H)-(+)-MK801 in the presence of in each case 10 μmole/l of the respective compound of formula I serves as a measure of the affinity of this compound for the (+)-MK801 binding site of the ionotropic NMDA receptor.

$IC_{50}$ values (concentration of the substituted compounds with 50% displacement of the radioactive ligand from its specific binding) were calculated according to the Law of Mass Action by means of non-linear regression from assays involving concentration ranges of these compounds of formula I. $K_i$ values were calculated from these $IC_{50}$ values by the Cheng-Prusoff equation (Y. Cheng, W. H. Prusoff, 1973, Biochem. Pharmacol., 22, pp. 3099–3108).

The results are shown in Tables 2 and 3.

TABLE 2

Molecular Biology Investigations

| Compound according to Example No. | Naloxone $K_i$ (μM) | MK801 $K_i$ (μM) |
|---|---|---|
| 1 | 0.24 | 0.6 |
| 2 | 0.2 | 3.9 |
| 3 | 0.06 | 1.7 |
| 4 | 50% | 5.2 |
| 5 | 0.8 | 1.6 |
| 6 | 20% | 11.1 |
| 7 |  | 5.3 |
| 8 | 0.4 | 1.4 |
| 9 | 0.3 | 4.5 |
| 11 |  | 2.8 |

The compounds according to the invention advantageously exhibit a very balanced ratio of μ-agonistic and NMDA-antagoniostic action (deviations between the corresponding $K_i$ values are in principle not greater than a factor of 10) compared to the compounds according to WO 00/06545 and are accordingly particularly suitable for treating neuropathic pain as well well as the aforementioned conditions.

TABLE 3

Molecular Biology Investigations

| Compound according to | MK801 Binding Ki (μM) | Human μ-OR Binding Ki (μM) |
|---|---|---|
| Example 1 | 0.57 | 0.21 |
| Comparison example 1 | 63.3 | 1.27 |
| Comparison example 2 | 8.7 | 0.38 |

The in vivo effectiveness was demonstrated in particular for the compound according to Example 1.

Inhibition of the Wind-Up phenomenon in Rats

NMDA antagonistic inhibit bit the increased firing rate of spinal neurons that can be induced by repetitive electrical stimulation. This phenomenon is described as the wind-up phenomenon (Chizh, B. A., and Headley P. M. (1994) Thyrotropin-releasing hormone (TRH)-induced facilitation of spinal neurotransmission: a role for NMDA receptors. Neuropharmacology, Vol. 33, 115–121).

The compound according to Example 1 was investigated according to the procedure described in the aforementioned literature citation in a dose of 21.5 mg/kg i.v. The compound inhibited the wind-up phenomenon in rats (70% inhibition) and thus exhibits an in vivo effect to be expected with a centrally available NMDA antagonism of a substance. The compound according to Comparison example 1 on the other hand at the same dose did not influence the wind-up phenomenon.

The compounds according to the invention fall under the general formula of application WO 00/06545, but are not specifically mentioned at any point in the application and are also not included in the preferred compounds there. They are clearly superior to the already disclosed compounds.

What is claimed is:

1. A substituted 4-phenyl-1-(1-phenylcyclohexyl)-1,2,3,6-tetrahydropyridine compound of formula I,

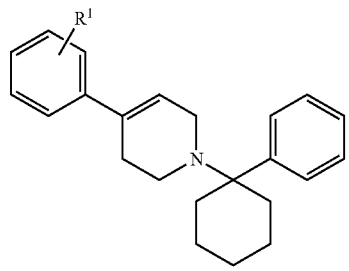

wherein $R^1$ denotes a branched or unbranched $C_1$–$C_5$-alkyl, a halogen other than chlorine at the 4-position, a branched or unbranched O—$C_1$–$C_5$-alkyl, a branched or unbranched S—$C_1$–$C_5$-alkyl, or a salt thereof of a physiologically compatible acid.

2. A compound according to claim 1, wherein $R^1$ denotes methyl, chlorine other than in the 4-position, fluorine, methoxy or methylsulfanyl.

3. A compound according to claim 1, which is:
4-(2-fluorophenyl)-1-(1-phenylcyclohexyl)-1,2,3,6-tetrahydropyridine,
4-(3-fluorophenyl)-1-(1-phenylcyclohexyl)-1,2,3,6-tetrahydropyridine,
4-(4-fluorophenyl)-1-(1-phenylcyclohexyl)-1,2,3,6-tetrahydropyridine
4-(2-methoxyphenyl)-1-(1-phenylcyclohexyl)-1,2,3,6-tetrahydropyridine,
4-(3-methoxyphenyl)-1-(1-phenylcyclohexyl)-1,2,3,6-tetrahydropyridine,
4-(4-methoxyphenyl)-1-(1-phenylcyclohexyl)-1,2,3,6-tetrahydropyridine,
4-(2-methylphenyl)-1-(1-phenylcyclohexyl)-1,2,3,6-tetrahydropyridine,
4-(3-methylphenyl)-1-(1-phenylcyclohexyl)-1,2,3,6-tetrahydropyridine,
4-(4-methylphenyl)-1-(1-phenylcyclohexyl)-1,2,3,6-tetrahydropyridine,
4-(2-methylsulfanylphenyl)-1-(1-phenylcyclohexyl)-1,2,3,6-tetrahydropyridine,
4-(2-chlorophenyl)-1-(1-phenylcyclohexyl)-1,2,3,6-tetrahydropyridine, or
a corresponding hydrochloride thereof.

4. A process for the production of a substituted 4-phenyl-1-(1-phenylcyclohexyl)-1,2,3,6-tetrahydropyridine of formula I according to claim 1, wherein the process comprises
(1) reacting a cyclohexanone of formula II with a 1,4-dioxa-8-aza-spiro[4,5]decane of formula III in the presence of titanium tetrachloride to form an enamine of formula IV,

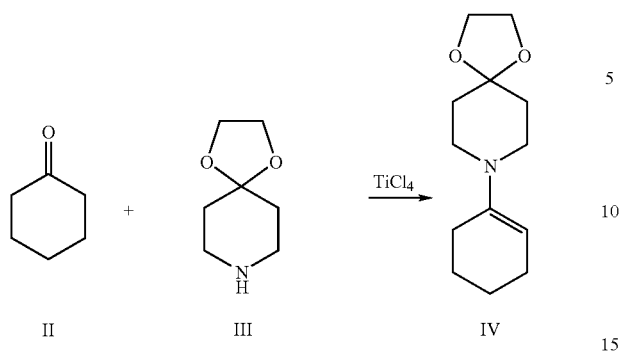

(2) reacting the enamine of formula IV with a phenyl-magnesium halide of formula V in the presence of trimethyl-chlorosilane to form an amine of formula VI, (3) hydrolyzing and precipitating the amine of formula VI as a hydrochloride of formula VII with concentrated hydrochloric acid

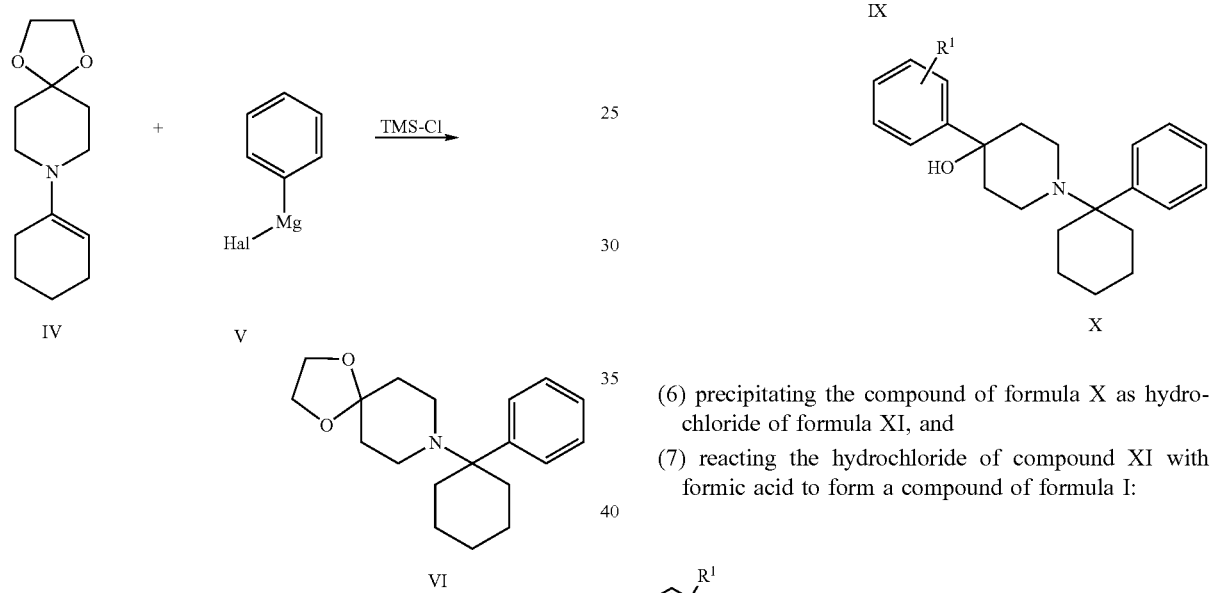

(4) converting the hydrochloride into a free base of formula VIII, (5) reacting the free base with a Grignard reagent of formula IX to form a compound of formula X,

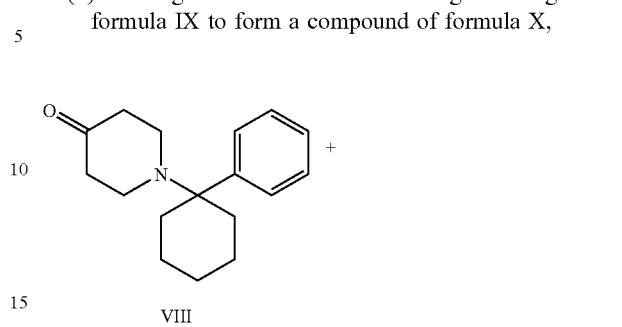

(6) precipitating the compound of formula X as hydrochloride of formula XI, and (7) reacting the hydrochloride of compound XI with formic acid to form a compound of formula I:

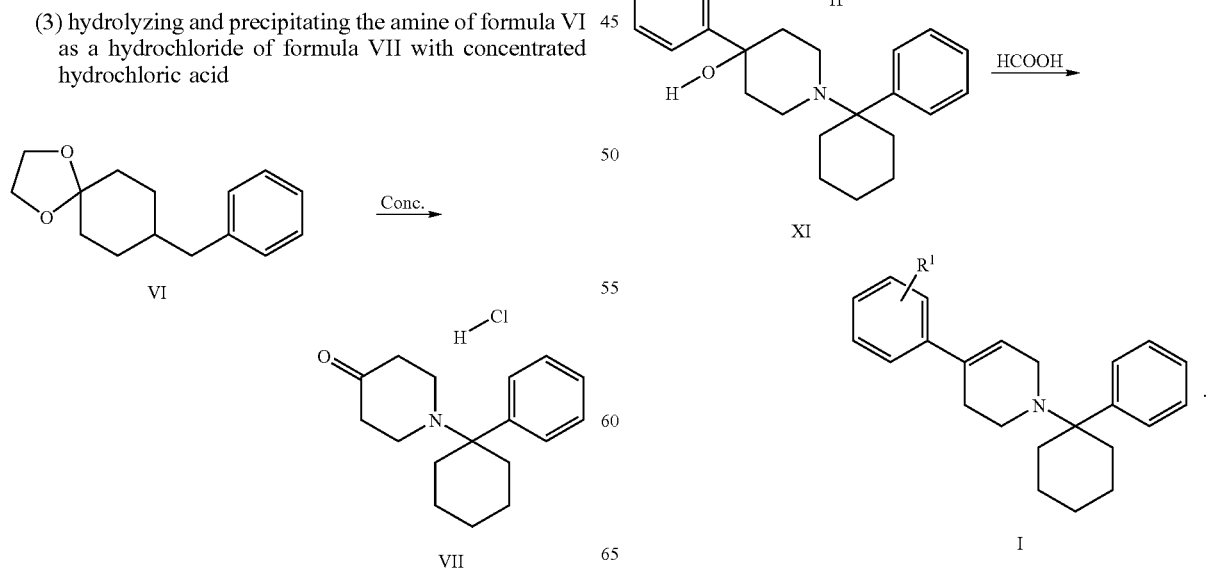

5. A process according to claim 4, further comprising purifying the compound of formula I.

6. A method according to claim 4, further comprising reacting the compound of formula I with a physiologically acceptable acid to form a physiologically acceptable salt.

7. A process for the production of a substituted 4-phenyl-1-(1-phenylcyclohexyl)-1,2,3,6-tetrahydropyridine of formula I according to claim 1, wherein the process comprises (1) reacting a cyclohexanone of formula II with a 1,4-dioxa-8-aza-spiro[4,5]decane of formula III in the presence of titanium tetrachloride to form an enamine of formula IV,

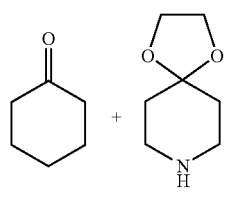 

II  III

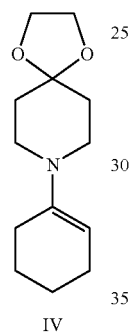

IV (2) introducing ethereal HCl to the enamine of formula IV, and reacting the enamine with a phenylmagnesium halide of formula V in the presence of ethereal HCl to form an amine of formula VI,

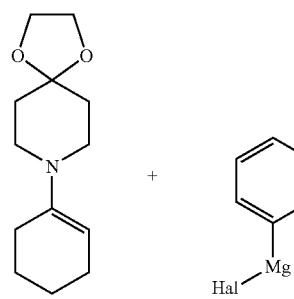 

IV  V

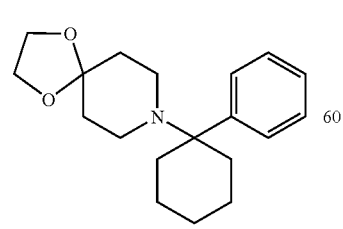

VI (3) hydrolyzing and precipitating the amine of formula VI as a hydrochloride of formula VII with concentrated hydrochloric acid,

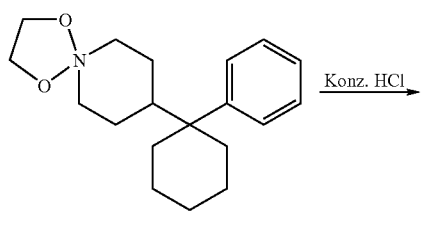 

VI

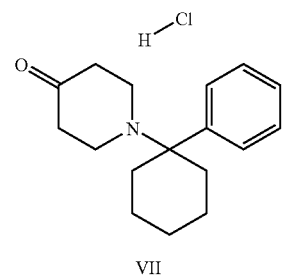

VII (4) converting the hydrochloride into a free base of formula VIII, (5) reacting the free base with a Grignard reagent of formula IX to form a compound of X:

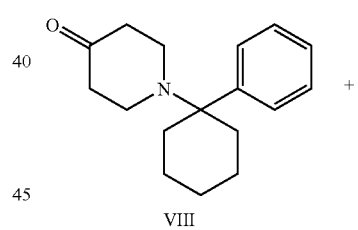

VIII

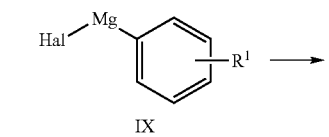

IX

X (6) precipitating the compound of formula X as a hydrochloride of formula XI, and
(7) reacting the hydrochloride of formula XI with formic acid to form a compound of formula I.

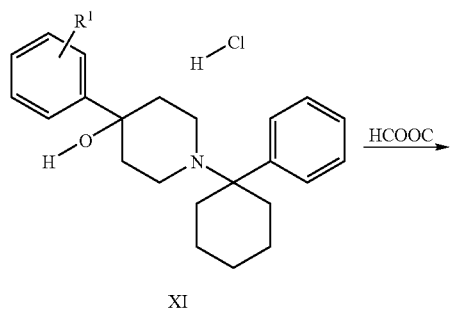

XI

HCOOC →

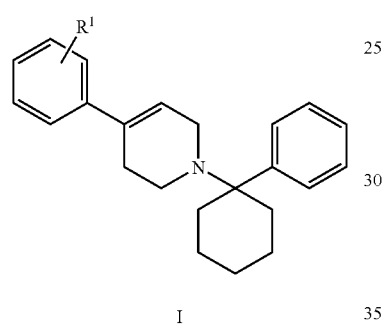

I

8. A process according to claim 7, further comprising purifying the compound of formula I.
9. A method according to claim 7, further comprising reacting the compound of formula I with a physiologically acceptable acid to form a physiologically acceptable salt.
10. A process for the production of a compound of formula I,

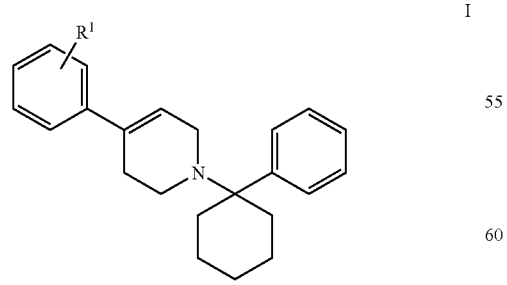

I wherein R¹ denotes a branched or unbranched $C_1$–$C_5$-alkyl, a halogen other than chlorine at the 4-position, a branched or unbranched O—$C_1$–$C_5$-alkyl, a branched or unbranched S—$C_1$–$C_5$-alkyl, wherein the process comprises
(1) reacting a cyclohexanone of formula II with a 1,4-dioxa-8-aza-spiro[4,5]decane of formula III in the presence of potassium cyanide and hydrochloric acid to form an aminonitrile of formula XII,

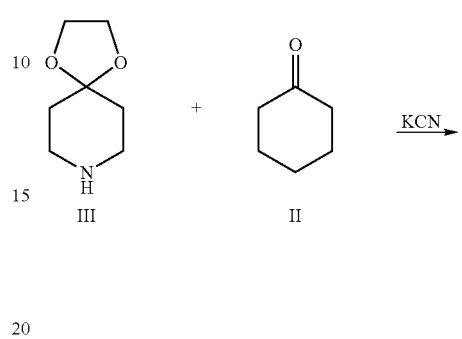

III    II    KCN →

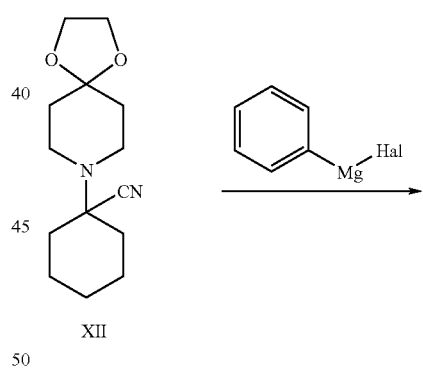

XII (2) reacting the aminonitrile of formula XII with a phenyl Grignard reagent to form an amine of formula VI, XII    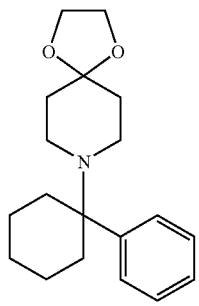

VI (3) hydrolyzing and precipitating the amine of formula VI as a hydrochloride of formula VII with concentrated hydrochloric acid, (4) converting the hydrochloride into a free base of formula VIII, (5) reacting the free base with a Grignard reagent of formula IX to form a compound of formula X:

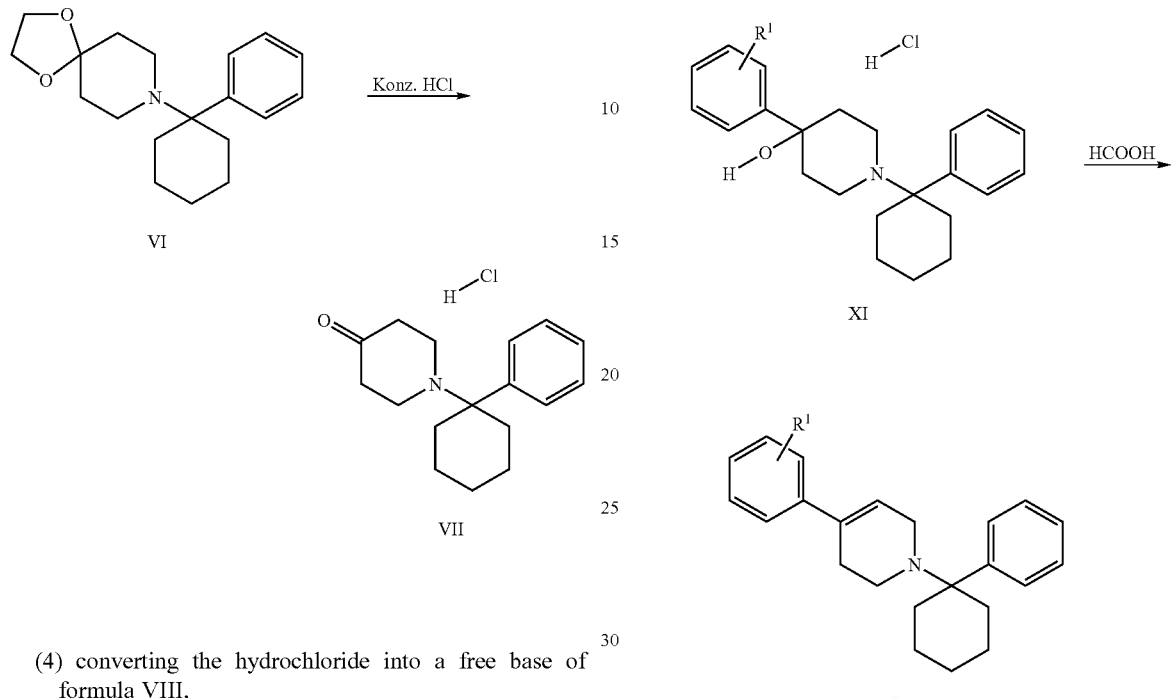

(6) precipitating the compound of formula X as a hydrochloride of formula XI, and (7) reacting the hydrochloride of formula XI with formic acid to form a compound of formula I.

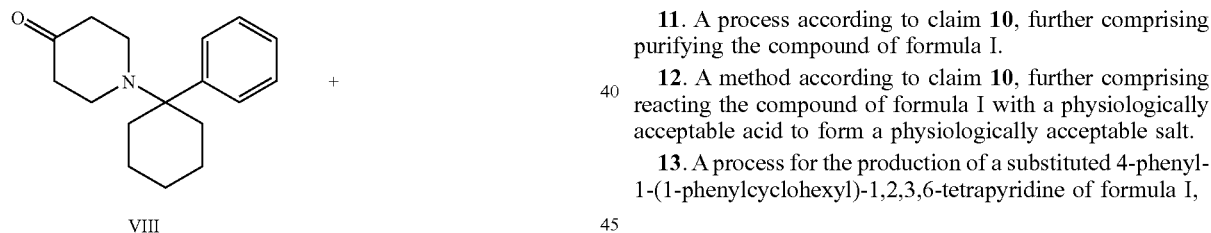

11. A process according to claim 10, further comprising purifying the compound of formula I.

12. A method according to claim 10, further comprising reacting the compound of formula I with a physiologically acceptable acid to form a physiologically acceptable salt.

13. A process for the production of a substituted 4-phenyl-1-(1-phenylcyclohexyl)-1,2,3,6-tetrapyridine of formula I,

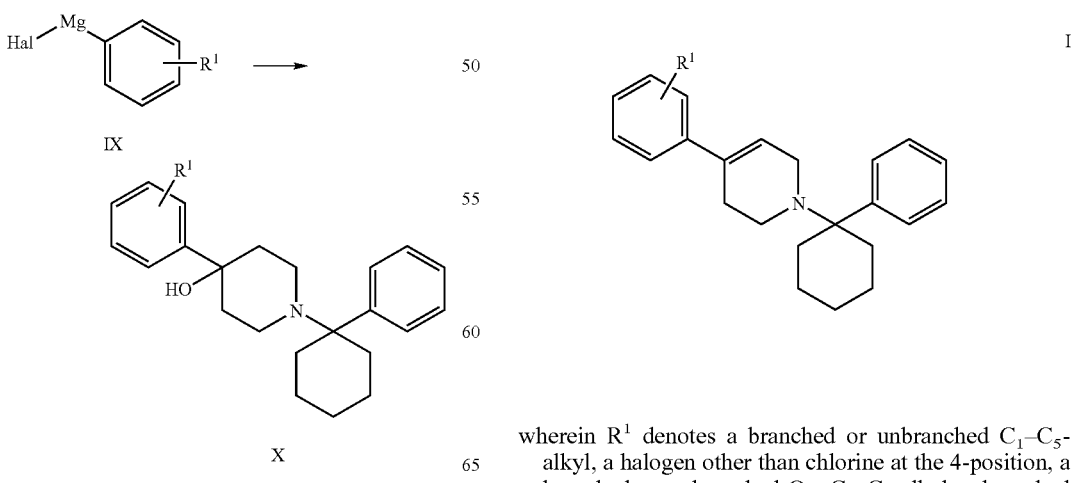

wherein $R^1$ denotes a branched or unbranched $C_1$–$C_5$-alkyl, a halogen other than chlorine at the 4-position, a branched or unbranched O—$C_1$–$C_5$-alkyl, a branched or unbranched S—$C_1$–$C_5$-alkyl, wherein the process comprises (1) reacting an N-tert.-butyloxycarbonyl-4-piperidone of formula XIII with a Grignard reagent of formula IX to form a compound of formula XIV:

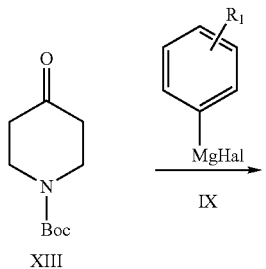

(2) removing the tert.-butyloxycarbonyl protective group from the compound of formula XIV with an acid, to obtain a compound of formula XV as a HCl salt,

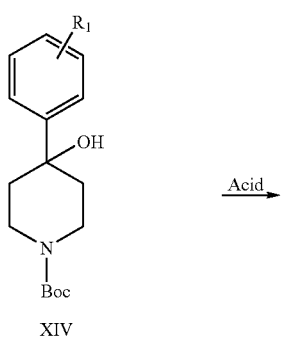

(3) reacting the HCl salt with titanium(IV) chloride and a cyclohexanone of formula II to form an enamine of formula XVI,

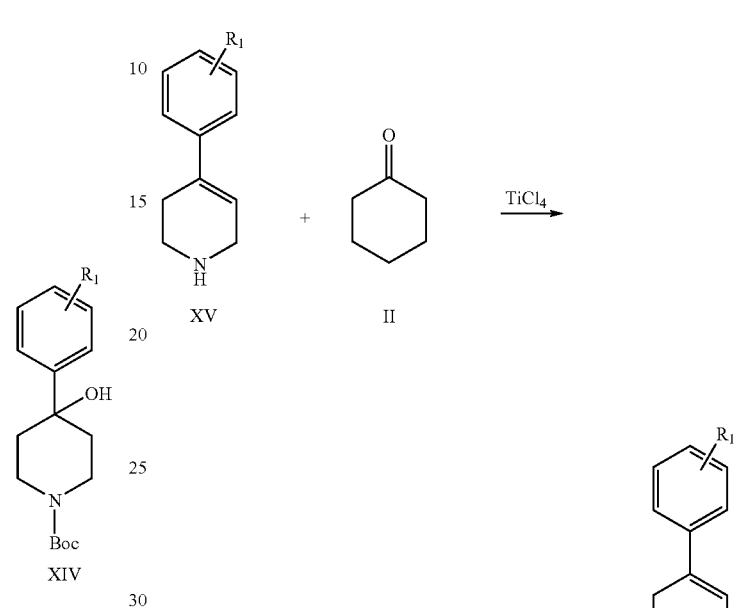

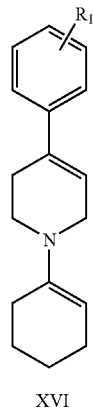

(4) reacting the enamine of formula XVI with a phenyl-magnesium halide in the presence of trimethylchlorosilane or ethereal HCl,

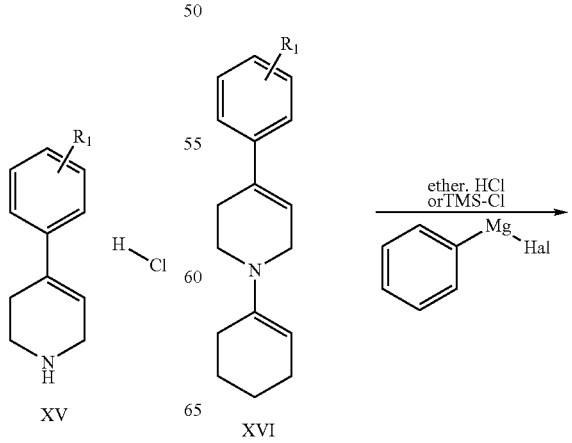

-continued

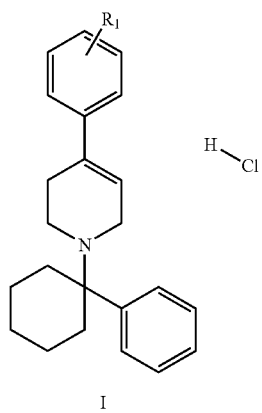

wherein a HCl salt of the compound of formula I is precipitated.

14. A process according to claim 13, further comprising purifying the compound of formula I.

15. A process according to claim 13, further comprising converting the HCl salt of formula I to a free base and reacting the free base to a physiologically acceptable acid.

16. A process according to claim 13, wherein the acid in step (2) is HCl, HBr, or formic acid, or a mixture of HBr and glacial acetic acid.

17. A pharmaceutical composition comprising at least one compound according to claim 1, and a pharmaceutically acceptable carrier.

18. A method for relieving pain, comprising administering a pharmaceutical composition of claim 17 to a patient in need thereof.

19. A method for the treatment of at least one disease selected from the group consisting of epilepsy, schizophrenia, cerebral ischaemia, and dementia, comprising administering a pharmaceutical composition of claim 17 to a patient in need thereof.

* * * * *